(12) United States Patent  (10) Patent No.: US 7,998,199 B2
Ben Nun  (45) Date of Patent: Aug. 16, 2011

(54) METHOD OF ANCHORING AN ACCOMMODATING INTRAOCULAR LENS ASSEMBLY

(75) Inventor: Joshua Ben Nun, Vitkin (IL)

(73) Assignee: Nulens, Ltd., Herzliya (IL)

( * ) Notice: Subject to any disclaimer, the term of this patent is extended or adjusted under 35 U.S.C. 154(b) by 0 days.

(21) Appl. No.: 12/906,774

(22) Filed: Oct. 18, 2010

(65) Prior Publication Data

US 2011/0082544 A1    Apr. 7, 2011

Related U.S. Application Data

(63) Continuation of application No. 11/734,180, filed on Apr. 11, 2007, now Pat. No. 7,854,764, which is a continuation of application No. 10/487,005, filed as application No. PCT/IL02/00693 on Aug. 21, 2002, now Pat. No. 7,220,279.

(30) Foreign Application Priority Data

Aug. 21, 2001 (IL) .......................................... 145015

(51) Int. Cl.
*A61F 2/16* (2006.01)
(52) U.S. Cl. ...................... 623/6.37; 623/6.44; 623/6.38
(58) Field of Classification Search .................. 623/6.11, 623/6.37, 6.45, 6.17, 6.13, 6.43, 6.44, 6.5
See application file for complete search history.

(56) References Cited

U.S. PATENT DOCUMENTS

| 3,950,082 A | 4/1976 | Volk |
|---|---|---|
| 4,122,556 A | 10/1978 | Poler |
| 4,254,509 A | 3/1981 | Tennant |
| 4,298,994 A | 11/1981 | Clayman |
| 4,340,979 A | 7/1982 | Kelman |
| 4,409,690 A | 10/1983 | Gess |
| 4,409,691 A | 10/1983 | Levy |
| 4,445,998 A | 5/1984 | Kanda et al. |

(Continued)

FOREIGN PATENT DOCUMENTS

EP    0 156 472 A    10/1985

(Continued)

OTHER PUBLICATIONS

Chu, Ralph Y. and Buliano, Megan, Accommodating IOLS by Ralph Chu et al, Cataract & Refractive Surgery Today, May 2004.

(Continued)

*Primary Examiner* — David H Willse
*Assistant Examiner* — Tiffany Shipmon
(74) *Attorney, Agent, or Firm* — Morgan Lewis & Bockius, LLP

(57) ABSTRACT

A method of anchoring an accommodating intraocular lens assembly in the posterior chamber of an eye includes the steps of, (1) introducing the first haptic portion, which includes a first anchor portion projecting therefrom, into the posterior chamber of the eye until the first anchor portion is anchored in the scleral wall at a desired location; and (2) moving the second haptic portion, which comprises a second anchor portion projecting therefrom, until the second anchor portion is anchored in the scleral wall on the opposite side of the lens from the first anchor portion and the lens structure is in contact with the collapsed natural lens, whereby the collapsed natural lens capsule will be prestressed and deform the lens body relative to and substantially independently of the haptics element in relation to the force the capsular unit applies directly or indirectly to the lens body along the optical axis.

5 Claims, 3 Drawing Sheets

U.S. PATENT DOCUMENTS

| | | |
|---|---|---|
| 4,446,581 A | 5/1984 | Blake |
| 4,494,254 A | 1/1985 | Lopez |
| 4,530,117 A | 7/1985 | Kelman |
| RE31,963 E | 8/1985 | Kelman |
| 4,556,998 A | 12/1985 | Siepser |
| 4,581,033 A | 4/1986 | Callahan |
| 4,589,147 A | 5/1986 | Nevyas |
| 4,591,358 A | 5/1986 | Kelman |
| 4,615,701 A | 10/1986 | Woods |
| 4,671,283 A | 6/1987 | Hoskin et al. |
| 4,676,794 A | 6/1987 | Kelman |
| 4,750,904 A | 6/1988 | Price, Jr. |
| 4,808,181 A | 2/1989 | Kelman |
| 4,842,601 A | 6/1989 | Smith |
| RE33,039 E | 8/1989 | Arnott |
| 4,865,601 A | 9/1989 | Caldwell et al. |
| 4,888,012 A | 12/1989 | Horn et al. |
| 4,892,543 A | 1/1990 | Turley |
| 4,932,966 A | 6/1990 | Christie et al. |
| 4,932,968 A | 6/1990 | Caldwell et al. |
| 4,957,505 A | 9/1990 | McDonald |
| 4,969,897 A | 11/1990 | Kalb |
| 4,976,732 A | 12/1990 | Vorosmarthy |
| 4,990,159 A | 2/1991 | Kraff |
| 5,078,742 A | 1/1992 | Dahan |
| 5,171,268 A | 12/1992 | Ting et al. |
| 5,176,701 A | 1/1993 | Dusek et al. |
| 5,275,623 A | 1/1994 | Sarfarazi |
| 5,282,851 A | 2/1994 | Jacob-LaBarre |
| 5,288,293 A | 2/1994 | O'Donnell, Jr. |
| 5,336,262 A * | 8/1994 | Chu .................. 128/898 |
| 5,346,502 A | 9/1994 | Estabrook et al. |
| 5,476,512 A | 12/1995 | Sarfarazi |
| 5,476,514 A | 12/1995 | Cumming |
| 5,476,515 A | 12/1995 | Kelman et al. |
| 5,480,426 A | 1/1996 | Chu |
| 5,484,447 A | 1/1996 | Waldock et al. |
| 5,489,302 A | 2/1996 | Skottun |
| 5,496,366 A | 3/1996 | Cumming |
| 5,522,891 A | 6/1996 | Klaas |
| 5,567,365 A | 10/1996 | Weinschenk et al. |
| 5,571,177 A | 11/1996 | Deacon et al. |
| 5,607,472 A | 3/1997 | Thompson |
| 5,628,795 A | 5/1997 | Langerman |
| 5,674,282 A | 10/1997 | Cumming |
| 5,684,637 A | 11/1997 | Floyd |
| 5,722,952 A | 3/1998 | Schachar |
| 5,752,960 A | 5/1998 | Nallakrishnan |
| 5,766,244 A | 6/1998 | Binder |
| 5,843,188 A | 12/1998 | McDonald |
| 5,871,455 A | 2/1999 | Ueno |
| 5,919,230 A | 7/1999 | Sambursky |
| 5,968,094 A | 10/1999 | Werblin et al. |
| 6,007,579 A | 12/1999 | Lipshitz et al. |
| 6,051,024 A | 4/2000 | Cumming |
| 6,110,202 A | 8/2000 | Barraquer et al. |
| 6,117,171 A | 9/2000 | Skottun |
| 6,129,759 A | 10/2000 | Chambers |
| 6,164,282 A | 12/2000 | Gwon et al. |
| 6,193,750 B1 | 2/2001 | Cumming |
| 6,197,057 B1 | 3/2001 | Peyman et al. |
| 6,197,059 B1 | 3/2001 | Cumming |
| 6,200,342 B1 | 3/2001 | Tassignon |
| 6,280,469 B1 | 8/2001 | Terry et al. |
| 6,280,471 B1 | 8/2001 | Peyman et al. |
| 6,299,618 B1 | 10/2001 | Sugiura |
| 6,299,641 B1 | 10/2001 | Woods |
| 6,342,073 B1 | 1/2002 | Cumming et al. |
| 6,387,126 B1 | 5/2002 | Cumming |
| 6,406,494 B1 | 6/2002 | Laguette et al. |
| 6,423,094 B1 | 7/2002 | Sarfarazi |
| 6,443,984 B1 | 9/2002 | Jahn et al. |
| 6,443,985 B1 | 9/2002 | Woods |
| 6,464,725 B2 | 10/2002 | Skottun |
| 6,488,708 B2 | 12/2002 | Sarfarazi |
| 6,494,910 B1 | 12/2002 | Ganem et al. |
| 6,494,911 B2 | 12/2002 | Cumming |
| 6,503,276 B2 | 1/2003 | Lang et al. |
| 6,506,212 B2 | 1/2003 | Zhou et al. |
| 6,520,691 B2 | 2/2003 | Nomura et al. |
| 6,524,340 B2 | 2/2003 | Israel |
| 6,554,860 B2 | 4/2003 | Hoffmann et al. |
| 6,570,718 B2 | 5/2003 | Nomura et al. |
| 6,596,026 B1 | 7/2003 | Gross et al. |
| 6,599,317 B1 | 7/2003 | Weinschenk, III et al. |
| 6,605,093 B1 | 8/2003 | Blake |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,739,722 B2 | 5/2004 | Laguette et al. |
| 6,749,634 B2 | 6/2004 | Hanna |
| 6,790,232 B1 | 9/2004 | Lang |
| 6,849,091 B1 | 2/2005 | Cumming |
| 6,960,231 B2 | 11/2005 | Tran |
| 6,972,033 B2 | 12/2005 | McNicholas |
| 7,008,449 B2 | 3/2006 | Willis et al. |
| 7,025,783 B2 | 4/2006 | Brady et al. |
| 7,037,338 B2 | 5/2006 | Nagamoto |
| 7,097,660 B2 | 8/2006 | Portney |
| 7,118,597 B2 | 10/2006 | Miller et al. |
| 7,122,053 B2 | 10/2006 | Esch |
| 7,137,994 B2 | 11/2006 | De Juan, Jr. |
| 7,220,279 B2 | 5/2007 | Nun |
| 7,261,737 B2 | 8/2007 | Esch et al. |
| 7,278,739 B2 | 10/2007 | Shadduck |
| 7,350,916 B2 | 4/2008 | Hong et al. |
| 7,815,678 B2 | 10/2010 | Nun |
| 7,842,087 B2 | 11/2010 | Nun |
| 7,854,764 B2 | 12/2010 | Nun |
| 2002/0103535 A1 | 8/2002 | Portney |
| 2002/0103537 A1 | 8/2002 | Willis et al. |
| 2003/0060881 A1 | 3/2003 | Glick et al. |
| 2003/0097177 A1 | 5/2003 | Tran |
| 2003/0109926 A1 | 6/2003 | Portney |
| 2003/0149480 A1 | 8/2003 | Shadduck |
| 2004/0073304 A1 | 4/2004 | Weinschenk, III et al. |
| 2004/0148022 A1 | 7/2004 | Eggleston |
| 2004/0169816 A1 | 9/2004 | Esch |
| 2004/0181279 A1 | 9/2004 | Nun |
| 2005/0090896 A1 | 4/2005 | Nun |
| 2005/0177229 A1 | 8/2005 | Boxer Wachler |
| 2006/0069431 A1 | 3/2006 | Graney et al. |
| 2006/0069433 A1 | 3/2006 | Nun |
| 2006/0074487 A1 | 4/2006 | Gilg |
| 2007/0027538 A1 | 2/2007 | Aharoni et al. |
| 2007/0088433 A1 | 4/2007 | Esch et al. |
| 2007/0129799 A1 | 6/2007 | Schedler |
| 2007/0129801 A1 | 6/2007 | Cumming |
| 2007/0185574 A1 | 8/2007 | Nun |
| 2007/0244561 A1 | 10/2007 | Nun |
| 2008/0004699 A1 | 1/2008 | Nun |
| 2008/0188930 A1 | 8/2008 | Mentak et al. |
| 2008/0300680 A1 | 12/2008 | Joshua |
| 2009/0198247 A1 | 8/2009 | Nun |
| 2009/0264998 A1 | 10/2009 | Mentak et al. |
| 2010/0121444 A1 | 5/2010 | Nun |

FOREIGN PATENT DOCUMENTS

| | | |
|---|---|---|
| EP | 1 321 112 A | 6/2003 |
| FR | 2 794 965 | 12/2000 |
| JP | 2005007029 | 1/2005 |
| TW | 523408 | 3/2003 |
| WO | WO 83/00998 | 3/1983 |
| WO | WO 94/28825 | 12/1994 |
| WO | WO 95/20367 | 8/1995 |
| WO | WO 98/05273 | 2/1998 |
| WO | WO 98/10717 | 3/1998 |
| WO | WO 99/62434 | 12/1999 |
| WO | WO 00/30566 | 6/2000 |
| WO | WO 00/61036 | 10/2000 |
| WO | WO 00/66037 | 11/2000 |
| WO | WO 01/08606 | 2/2001 |
| WO | WO 01/60286 | 8/2001 |
| WO | WO 02/065951 | 8/2002 |
| WO | WO 03/000154 | 1/2003 |
| WO | WO 03/015669 | 2/2003 |

| | | |
|---|---|---|
| WO | WO 2005/104994 | 11/2005 |
| WO | WO 2006/040759 | 4/2006 |
| WO | WO 2006/103674 | 10/2006 |
| WO | WO 2008/023379 | 2/2008 |
| WO | WO 2008/097915 | 8/2008 |
| WO | WO 2008/107882 | 9/2008 |
| WO | WO 2009/122409 | 10/2009 |
| WO | WO 2010/010565 | 1/2010 |

OTHER PUBLICATIONS

Notification of Transmittal of the International Preliminary Report on Patentability for PCT/IL2009/000728 filed Jul. 26, 2009 (having a priority date of Jul. 24, 2008).

* cited by examiner

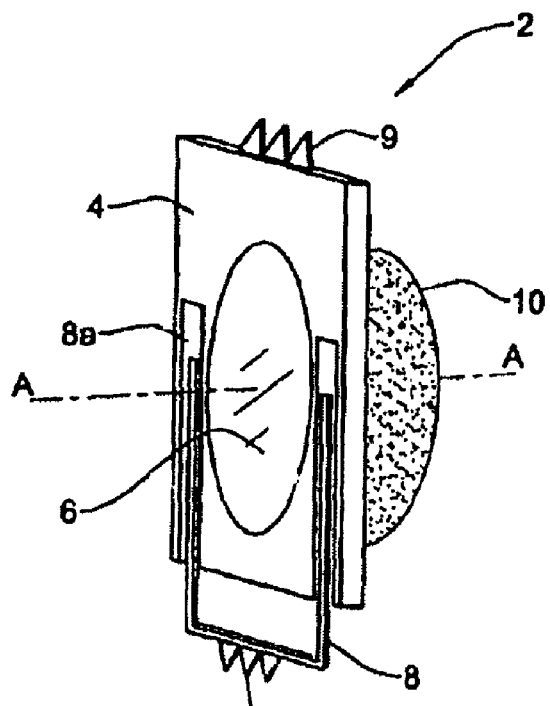
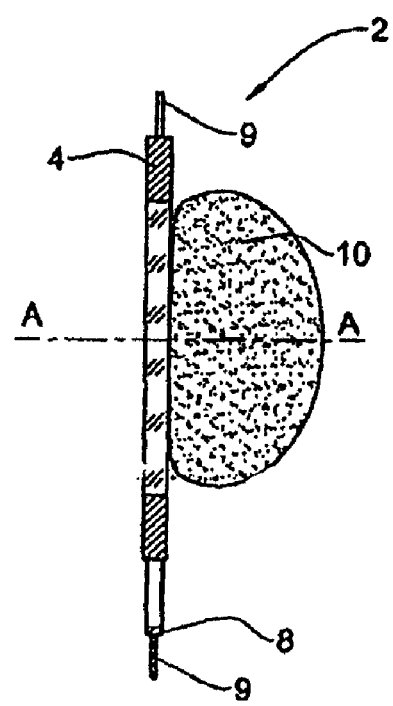
FIG. 1A
FIG. 1B
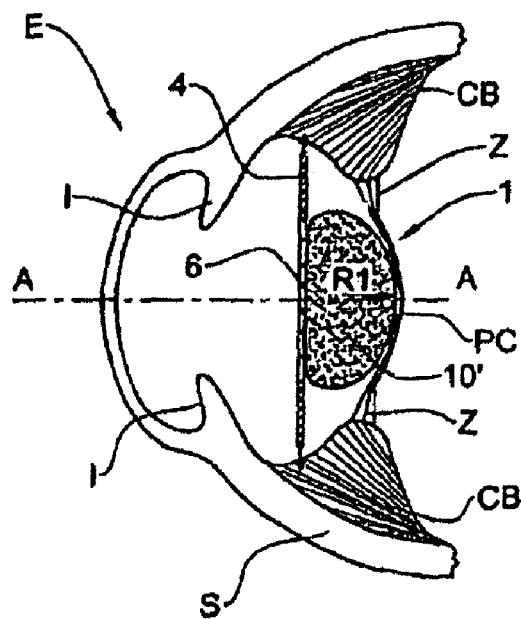
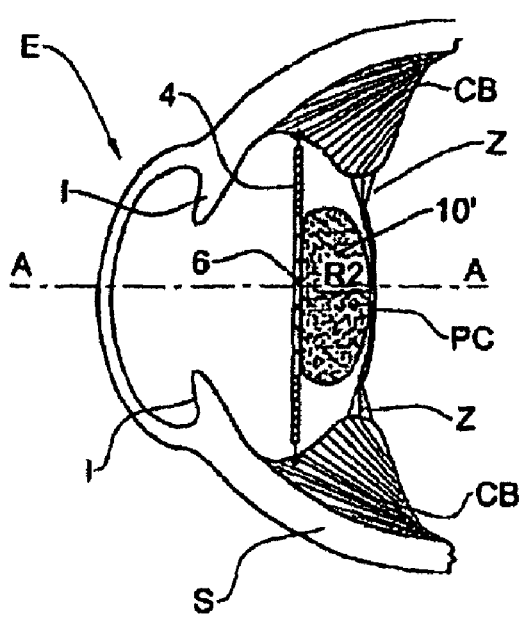
FIG. 2A
FIG. 2B

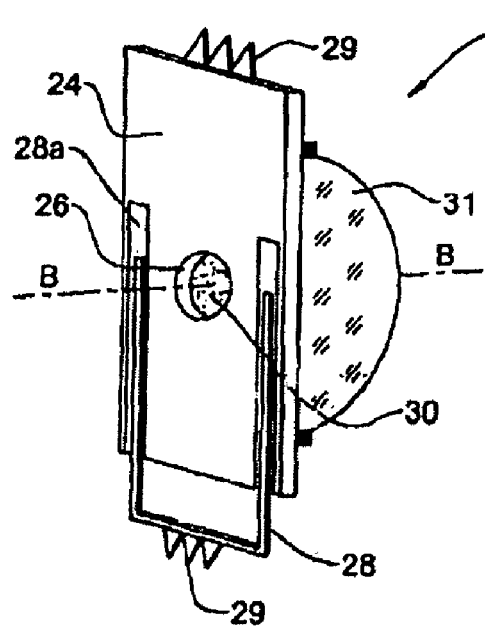
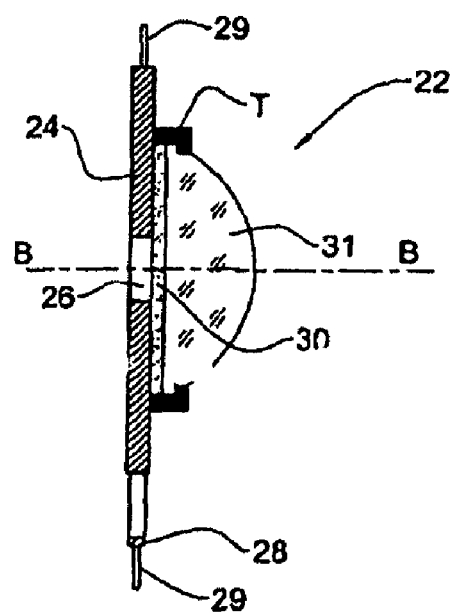
FIG. 3A          FIG. 3B
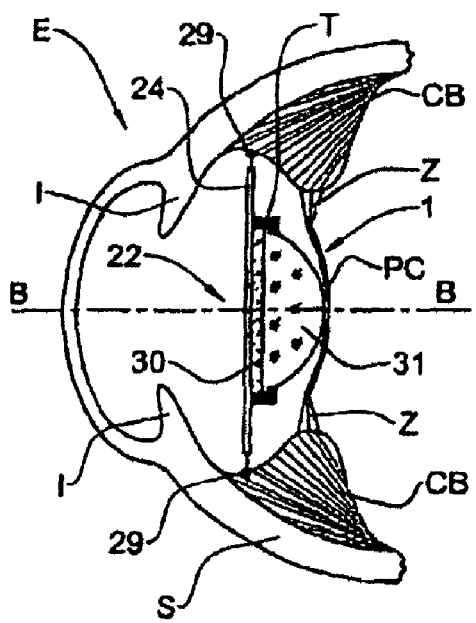
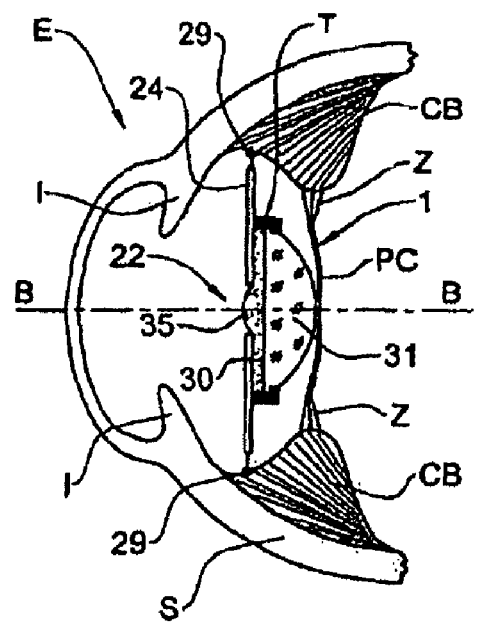
FIG. 4A          FIG. 4B

METHOD OF ANCHORING AN ACCOMMODATING INTRAOCULAR LENS ASSEMBLY

CROSS-REFERENCE TO RELATED APPLICATIONS

This application is a Continuation Application of U.S. patent application Ser. No. 11/734,180, filed on Apr. 11, 2007, which issued on Dec. 21, 2010 as U.S. Pat. No. 7,854,764, which was a Continuation Application of U.S. patent application Ser. No. 10/487,005, filed on Feb. 19, 2004 now U.S. Pat. No. 7,220,279, which was a national stage application of PCT/IL02/00693 filed Aug. 21, 2002, claiming priority to IL 145015 filed Aug. 21, 2001, all of which are incorporated herein by reference in their entirety.

FIELD OF THE INVENTION

This invention relates to intraocular lenses, and in particular, to accommodating intraocular lenses capable of focusing on objects located at various distances therefrom.

BACKGROUND OF THE INVENTION

The natural lens of a human eye is a transparent crystalline body, which is contained within a capsular bag located behind the iris and in front of the vitreous cavity in a region known as the posterior chamber. The capsular bag is attached on all sides by fibers, called zonules, to a muscular ciliary body. At its rear, the vitreous cavity, which is filled with a gel, further includes the retina, on which light rays passing through the lens are focused. Contraction and relaxation of the ciliary bodies changes the shape of the bag and of the natural lens therein, thereby enabling the eye to focus light rays on the retina originating from objects at various distances.

Cataracts occur when the natural lens of the eye or of its surrounding transparent membrane becomes clouded and obstructs the passage of light resulting in various degrees of blindness. To correct this condition in a patient, a surgical procedure is known to be performed in which the clouded natural lens, or cataract, is extracted and replaced by an artificial intraocular lens. During cataract surgery, the anterior portion of the capsular bag is removed along with the cataract, and the posterior portion of the capsular bag, called the posterior capsule, is sometimes left intact to serve as a support site for implanting the intraocular lens. Such lenses, however, have the drawback that they have a fixed refractive power and are therefore unable to change their focus.

Various types of intraocular lenses having the capability of altering their refractive power have been suggested in an effort to duplicate the performance of the natural lens within the eye. Such accommodating intraocular lenses, as they are known in the art, have a variety of designs directed to enable the patient to focus on, and thereby clearly see, objects located at a plurality of distances. Examples may be found in such publications as U.S. Pat. No. 4,254,509, U.S. Pat. No. 4,932,966, U.S. Pat. No. 6,299,641, and U.S. Pat. No. 6,406,494.

U.S. Pat. No. 5,489,302 discloses an accommodating intraocular lens for implantation in the posterior chamber of the eye. This lens comprises a short tubular rigid frame and transparent and resilient membrane attached thereto at its bases. The frame and the membranes confine a sealed space filled with a gas. The frame includes flexible regions attached via haptics to the posterior capsule. Upon stretching of the capsule by the eye's ciliary muscles, the flexible regions are pulled apart, thereby increasing the volume and decreasing the pressure within the sealed space. This changes the curvature of the membranes and accordingly, the refractive power of the lens.

U.S. Pat. No. 6,117,171 discloses an accommodating intraocular lens which is contained inside an encapsulating rigid shell so as to make it substantially insensitive to changes in the intraocular environment. The lens is adapted to be implanted within the posterior capsule and comprises a flexible transparent membrane, which divides the interior of the intraocular lens into separate front and rear spaces, each filled with a fluid having a different refractive index. The periphery of the rear space is attached to haptics, which are in turn attached to the posterior capsule. Upon stretching of the capsule by the eye's ciliary muscles, the haptics and hence this periphery is twisted apart to increase the volume of rear space and changes the pressure difference between the spaces. As a result, the curvature of the membrane and accordingly, the refractive power of the lens changes.

BRIEF SUMMARY OF THE INVENTION

The present invention suggests an accommodating lens assembly having an optical axis and being adapted to be implanted in a posterior chamber of an eye having a capsular unit located therein. The assembly comprises a rigid haptics element adapted to secure the assembly within said posterior chamber outside the capsular unit, the element being transparent at least in a region around the axis. The assembly further comprises a resilient body adapted to operate as a lens with a radius of curvature, when pressed up against the region of the rigid element by an axial force applied thereto by the capsular unit, whereby a change in said force causes a change in the radius of curvature.

The term "capsular unit", as it is used in the present description and claims, refers to the posterior capsule, the zonules, and the ciliary body, which are interconnected and act in unison, forming in accordance with the present invention, a kind of cable whose varying tension provides the axial force applied to and utilized by the lens assembly of the present invention to achieve accommodation.

The assembly of the present invention is directed to substitute for a natural lens after its removal from the eye, not only by enabling the eye to see after implantation of the assembly, but also by enabling it to accommodate and thereby bring into focus objects located at a continuum of distances. In order to achieve the latter, the assembly is designed to be fixed in the posterior chamber, with the resilient body axially abutting the posterior capsule. The resilient body may be attached to the haptic element or may simply be held in place up against the element by the tension of the capsular unit.

The lens assembly of the present invention utilizes the natural compression and relaxation of the capsular unit to impart an axial force on the resilient body in order to cause it to act as a lens whose radius of curvature, and therefore the refractive power it provides, varies depending on the magnitude of the force. In this way, the lens assembly cooperates with the natural operation of the eye to accommodate and enable the eye to clearly see objects at different distances.

The haptics element of the assembly according to the present invention may adopt any of a variety of designs known in the art, e.g. it may be curved or it may be in the form of a plate, which spans a plane essentially perpendicular to the optical axis of the assembly. In addition to the region, the haptics element may be completely transparent. The region of the element may be in the form of a transparent component, such as a clear panel or another lens which may have such a curvature and index of refraction as to enhance the accommodating capability of the lens assembly.

The haptics element may have a hollow space formed in its transparent region. This hollow space is adapted to allow the resilient body to bulge through the space in response to said force. This enables the lens assembly to provide a range of refractive power (i.e. the accommodating capability) depending on the bulge's radius of curvature, which is determined and may be varied by the magnitude of the force applied by the capsular unit.

The haptics element of the lens assembly of the present invention is adapted to securely fix the assembly in front of the capsular unit in the posterior chamber of the eye. It is essential that the haptics element maintain a substantially immovable position. To this end, the haptics element is preferably adapted to be fixed to the scleral wall of the eye in two or more places in the regions between the iris and the ciliary body. To achieve the latter, the haptics element preferably comprise anchoring means, such as in the form of teeth. One example of such means is described in co-pending Israel patent application no. 141529.

Implantation of the lens assembly in accordance with the present invention may be achieved using equipment and techniques that are conventional and well known in the art. However, in order to facilitate the implantation and anchoring of the assembly in the eye, the haptics element of the assembly of the present invention preferably also includes at least one extendible member at its periphery. For example, the haptics element in the form of a plate discussed above may have a telescoping end which is only extended after the assembly has been inserted into the eye and has been positioned at the anchoring site. This extendible member may also be provided with anchoring means attached thereto. The extendible member serves to keep the assembly small enough to insert into the eye until its securing is desired. The extendible member, such as the telescoping end, may be passive or may be spring biased being compressed to enable implantation and released to maintain anchoring by a resisting force.

The haptics element of the lens assembly in accordance with the present invention may be made of a variety of possible rigid materials suitable for invasive medical use and known in the art to be used in the formation of haptics.

The resilient body of the accommodating lens assembly in accordance with the present invention may be made of any suitable deformable material, such as silicone or hydrogel, having an index of refraction different from the gel within the eye. The resilient body must not necessarily be made of a single component or material. For example, the body may be in the form of a sac filled with a fluid or gel. However, in the case of such a sac, for example, it is essential the periphery of the body be made with a unitary material so that the fluctuating internal pressure of the eye does not affect the sac in an anisotropic manner, which would unpredictably affect the vision provided by the assembly.

The resilient body of the accommodating lens assembly in accordance with the present invention may have a variety of shapes so long as the shape has or is able to achieve a radius of curvature and thereby perform as a lens. For example, in the case when the haptics element is curved and solid (i.e. is devoid of a hollow space in said region), the resilient body may have such shapes as a sphere which, when pressed against its haptics element, takes on the shape of a double convex lens. Also, if the haptics element is flat like a plate, for example, the planar side of a hemispherical resilient body may be pressed up against it to act as a plano-convex lens. As another example, if the haptics element is flat and comprises a hollow space, such as an aperture or a cavity, the resilient body having a bi-planar shape, such as that of a solid circular disc, may be pressed up against the element since the force applied by the capsular unit will cause it to bulge into the aperture or cavity and attain, thereby, a radius of curvature.

The accommodating lens assembly in accordance with the present invention may further comprise a rigid piston member, which sandwiches the resilient body between it and the haptics element, and which is designed to be pushed by the force and, in response, to cause the resilient body to take on a desired curved shape. The piston member is transparent at least in a region around the axis and is movable along the axis with respect to the element. One or both of the haptics element and the piston member have a hollow space in their transparent region to allow the resilient body to bulge through the space in response to the force.

The hollow spaces formed in the haptics element and/or the piston member in preferred embodiments of the lens assembly in accordance with the present invention, may have various designs such as circular blind or through holes. Preferable, these spaces are large enough that their periphery is far from the optical axis so as not to substantially affect light passing thereabout by causing diffraction and other such undesired optical effects. Also, in order to minimize such optical disturbances, if a hollow space is formed within the piston member, the haptics element may be devoid of such a space and vice versa.

The piston member of the accommodating lens assembly of the present invention may be made of any of a variety of rigid biocompatible materials. The piston member may also have any of a variety of designs, such as a plano-convex design with the convexly curved side abutting the capsular unit so as to contribute to the range of refractive power which may be achieve by the assembly. Clearly, in the latter case, the transparent region of the piston member, like the resilient body, must have an index of refraction different from the natural gel surrounding the assembly when implanted in the eye. The radius of curvature and the index of refraction of the piston member may be adjusted and chosen in numerous ways to arrive at lens assemblies having various ranges of refractive power and degrees of sensitivity to the force applied by the capsular unit.

The advantages provided by the accommodating lens assembly of the present invention abound, particularly because of it is designed to be positioned in the eye completely outside of the posterior capsule. One advantage, for example, is that the lens assembly does not undesirably stretch and consequently harm the capsule. Also, the lens assembly does not need to conform to the size or shape of the capsule, and is therefore free to take on a larger variety of designs. Furthermore, the capsule is sometimes damaged during the surgery to remove the natural lens, but the lens assembly of the present invention does not require that the capsule be completely intact in the form of a bag but merely that it remain reliably connected as part of the capsular unit. Another advantage arising from the lens assembly being positioned outside of the posterior capsule is that it remains unaffected by the permanent and unpredictable constriction that the capsule inevitably undergoes due to scarring following the surgery for removal of the natural lens.

In addition to the above, the lens assembly of the present invention offers advantages such as a simple and inexpensive construction. The lens assembly of the present invention also provides the ability to accommodate within a vast range of refractive power, including the full range provided by the natural eye. Also, the lens assembly provides means for varying its sensitivity in response to the force applied by the capsular unit.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1A is a plan view of an accommodating lens assembly in accordance with the present invention;

FIG. 1B is a side view of the accommodating lens assembly shown in FIG. 1A;

FIG. 2A shows the accommodating lens assembly of FIGS. 1A and 1B as implanted in an eye;

FIG. 2B shows the accommodating lens assembly of FIGS. 1A and 1B in operation after it has been implanted in an eye as in FIG. 2A;

FIG. 3A is a plan view of another embodiment of an accommodating lens assembly in accordance with the present invention;

FIG. 3B is a side view of the accommodating lens assembly shown in FIG. 3A;

FIG. 4A shows the accommodating lens assembly of FIGS. 3A and 3B as implanted in an eye;

FIG. 4B shows the accommodating lens assembly of FIGS. 3A and 3B in operation after it has been implanted in an eye as in FIG. 4A;

DETAILED DESCRIPTION OF THE INVENTION

Figure 5A:
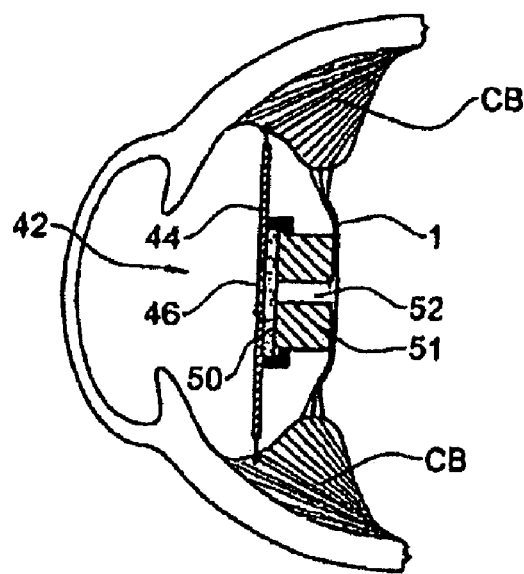
FIG. 5A shows yet another embodiment of an accommodating lens assembly in accordance with the present invention as implanted in the eye.

The subsequent description and figures refer to different examples of an accommodating lens assembly of the present invention and its functional position as implanted in a human eye E. As shown in FIGS. 2A, 2B, 4A, 4B, 5A, and 5B, the eye E, which is filled with natural gel (not shown) having an index of refraction of about 1.3, comprises a scleral wall S, an iris, and a retina R (not shown). The eye E further includes a ciliary body CB, from which extend zonules Z connected to a posterior capsule PC. These last three parts of the eye E constitute the capsular unit 1.

One example of an accommodating lens assembly in accordance with the present invention adapted for implantation within the eye E is shown in FIG. 1A in plan view and in FIG. 1B from a side view. The accommodating lens assembly 2 has an optical axis A-A and comprises a rigid haptics plate 4 having a first lens 6 made of a rigid material having an index of refraction higher than that of water. The plate 4 further includes a telescoping haptics member 8, which is slidably biased in grooves 8a so as to be extendible in a plane perpendicular to the optical axis A-A. The plate 4 and the telescoping member 8 have teeth 9 projecting therefrom for anchoring the first lens assembly 2 within the eye E.

The lens assembly 2 further comprises a silicone ball 10 attached to the plate 4 so as to be located on the axis A-A. The silicone ball 10 also has an index of refraction higher than that of water.

As is shown in FIGS. 2A and 2B, the haptics plate 4 of the assembly 2 is anchored, using the teeth 9, to the eye's scleral wall S at two locations between the ciliary body CB and the iris I. The anchoring is done by first inserting the teeth 9 on the plate 4 to the desired point in the scleral wall S, and then extending the telescoping member 8 until its teeth 9 enter the opposing side of the scleral wall S. The silicone ball 10 directly contacts the capsular unit 1, which is stretched around the ball 10 and transforms it into a second plano-convex lens 10' as shown in FIG. 2A with a radius of curvature R1.

In operation, upon contraction and relaxation by muscles of the ciliary body CB, tension in the capsular unit 1 will change and a variable force proportional to the tension will be applied to the silicone ball 10 along axis A-A. FIG. 2B shows an increase in tension in the capsular unit 1 compared to FIG. 2A upon relaxation of the ciliary body CB. The increase in tension applies a forward force along the axis in the direction of the iris I. This force causes the lens 10' to further deform and increase its radius of curvature from R1 to R2. This increase in radius will enable the eye E to focus on far objects by adjusting the assembly's focal plane until it resides on the retina. Clearly, the reverse may be done in which the ciliary body contracts, reducing the radius to focus on objects at near distances from the eye E.

Another example of an accommodating lens assembly 22 for implantation within a human eye E in accordance with the present invention is shown in a preferred embodiment in FIG. 3A in plan view and in FIG. 3B from a side view.

The accommodating lens assembly 22 has an optical axis B-B and comprises a rigid haptics plate 24, similar to that included in the lens assembly 2, and having a circular aperture 26. The plate 24 further includes a telescoping member 28, which is slidably biased in grooves 28a so as to be extendible. The plate 24 and the telescoping member 28 have teeth 29 projecting therefrom for anchoring the lens assembly 22 within the eye. The plate further includes a hollow, central cylindrical tube portion T extending around axis B-B. The tube portion T is concentric with the aperture 26 but has about double the diameter.

The accommodating lens assembly 22 further comprises a silicone disc 30 received within the tube portion T so as to occupy only a part of its axial dimension. The disc 30 has an index of refraction higher than that of water.

The lens assembly 22 also includes a rigid, plano convex lens 31 having a diameter slightly smaller than that of the tube portion T but greater than that of the aperture 26. The lens 31, which is designed to function like a piston by transferring an applied force to the disc 30, is received within the tube portion T to fill the space left unoccupied by the disc 30 and to press, with its planar face, the disc 30 up against the plate 24. The plano-convex lens 31 has a fixed radius of curvature and an index of refraction higher than that of water.

FIGS. 4A and 4B show the haptics plate 24 of the assembly 22 anchored, using the teeth 29, to the eye's scleral wall S at two locations, each being between the ciliary body CB and the iris I. The silicone disc 30 is sandwiched between the haptics plate 24 and the lens 31, which directly contacts the capsular unit 1 with its convex side.

In operation, upon contraction and relaxation by muscles of the ciliary body CB, tension in the capsular unit 1 will change and apply a force to the lens 31 along axis B-B. FIG. 4B shows an increase in tension in the capsular unit 1 compared to FIG. 4A, which occurs upon relaxation of the ciliary body CB. This increase in tension applies a forward force on the lens 31 along the axis in the direction of the iris I. The applied force pushes the lens 31, which functions like a piston and presses, in turn, on the silicone disc 30, causing it to protrude from the aperture 26 in the form of a bulge 35 having a radius of curvature depending on the force. The bulge 35 serves to add to the refractive power afforded by the convex curvature of lens 31. In this way, using the lens assembly 22, the eye E is given the ability to focus on nearer objects by changing the magnitude of the applied force and hence the radius of the bulge 35 until the object is focused on the retina R.

Figure 5B:
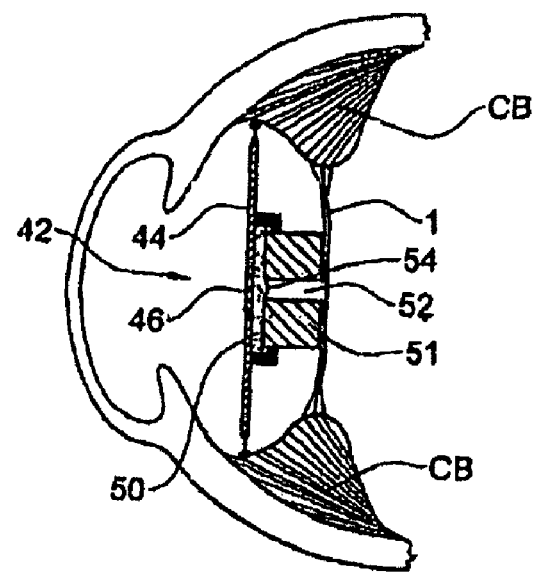
FIG. 5B shows the accommodating lens assembly of FIG. 5A in operation in the eye.

Yet another example of a lens assembly 42 in accordance with the present invention for implantation into the eye E is shown in a preferred embodiment in FIGS. 5A and 5B. The lens assembly 42 is similar to the lens assembly 22 in that it comprises a haptics plate 44 with an aperture which is occupied by a rigid lens 46, similarly to lens 6 in FIG. 1A. Furthermore, the lens assembly 42 comprises a piston member 51. However, the piston member 51 has a cylindrical cavity 52 formed therein, into the silicone disc 50 is adapted to bulge. The member 51 is adapted transfer an axial force applied by the capsular unit 1 to silicone disc 50 sandwiched between the member 51 and the plate 44. In this way, the piston member 51 is similar to plano-convex lens 31 shown e.g. in FIG. 4A, but differs in that it does not have the additional ability to operate as a lens.

In operation, the piston member 51 of the lens assembly 42 transfers the axial force, created thereon by changes of tension in the capsular unit 1, to the silicone disc 50, causing it to faun a bulge 54, which protrudes back into the cavity 52. The bulge 54 has a radius of curvature whose value varies depending on the magnitude of the force. As in the previously described embodiment, the bulge 54 serves to provide the assembly 42 with a refractive power, whose magnitude can be varied by the force applied by the capsular unit 1 and controlled by the contraction and relaxation of muscles in the eye's ciliary body CB.

Although the present invention and its advantages have been described in detail, it should be understood that various changes, substitutions and alterations can be made herein without departing from the spirit and scope of the invention as defined by the appended claims. For example, while implantation of the lens assembly in humans is described, the assembly may clearly also be applicable to other animals. Clearly, any and all possible permutations and/or combinations of different features as described above are within the scope of the present invention.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of anchoring an accommodating intraocular lens assembly in the posterior chamber of an eye, the lens assembly having an optical axis that corresponds with the visual axis of a human eye, the posterior chamber including a ciliary sulcus and a capsular unit with a collapsed natural lens capsule located therein, the assembly comprising a substantially rigid haptics element comprising first and second haptic portions with outermost portions, comprising first and second anchor portions with a plurality of teeth rigid enough to penetrate the scleral wall, which, when the teeth are anchored in the scleral wall, define a plane that intersects the visual axis of the eye, said haptics element securing said accommodating lens assembly within the posterior chamber outside the collapsed natural lens capsule, the haptics element allowing light to be transmitted therethrough at least in a region around said optical axis, and a lens structure that includes at least a resilient lens body located at least partially along the visual axis when the lens assembly is anchored in the posterior chamber of the eye, the method comprising the steps of:
  a. introducing the first haptic portion, which comprises said first anchor portion including a plurality of teeth projecting therefrom, into the posterior chamber of the eye until said teeth are anchored in the scleral wall at a desired location; and
  b. moving the second haptic portion, which comprises a second anchor portion including a plurality of teeth projecting therefrom, until said teeth are anchored in the scleral wall on the opposite side of the lens from the first anchor portion and the lens structure is in contact with the collapsed natural lens, whereby the collapsed natural lens capsule will be prestressed and deform the lens body relative to the haptics element in relation to the force the lens capsule applies directly or indirectly to the lens body along the optical axis.

2. The method of claim 1, wherein the haptic portions further comprise a plate with first and second telescoping members, the first member extending outwardly from the outer periphery of the lens in a first direction and the second member extending from the outer periphery of the lens in a direction opposite the first member, and the step of moving the second haptic portion further comprises extending the second telescoping member.

3. The method of claim 1, wherein the lens structure further comprises a resilient lens body positioned between the haptics element and the collapsed natural lens capsule after the lens assembly is anchored in place.

4. The method of claim 1, wherein the lens structure further comprises a resilient lens body and a rigid lens body, whereby the resilient lens is positioned between the rigid lens body and the haptics element after the lens assembly is anchored in place.

5. The method of claim 1, wherein the lens structure further comprises a resilient lens body and a rigid piston member with a cylindrical cavity formed therethrough, whereby the resilient lens body is positioned between the rigid piston member and the haptics element after the lens assembly is anchored in place.

* * * * *